(12) United States Patent
Cozzi

(10) Patent No.: US 11,224,226 B2
(45) Date of Patent: *Jan. 18, 2022

(54) DISINFECTING COMPOSITION COMPRISING SILVER IONS AND A QUATERNARY SALT

(71) Applicant: 99 HOLDING S.A.R.L., Luxembourg (LU)

(72) Inventor: Renato Cozzi, Corbetta (IT)

(73) Assignee: 99 HOLDING S.A.R.L., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/324,612

(22) PCT Filed: Jul. 8, 2015

(86) PCT No.: PCT/IB2015/055170
§ 371 (c)(1),
(2) Date: Jan. 6, 2017

(87) PCT Pub. No.: WO2016/005922
PCT Pub. Date: Jan. 14, 2016

(65) Prior Publication Data
US 2017/0202224 A1    Jul. 20, 2017

(30) Foreign Application Priority Data

Jul. 9, 2014 (IT) .......................... MI2014A001251

(51) Int. Cl.
| | | |
|---|---|---|
| *A01N 59/16* | (2006.01) | |
| *A01N 33/12* | (2006.01) | |
| *A01N 59/00* | (2006.01) | |
| *A01N 25/22* | (2006.01) | |
| *A01N 25/30* | (2006.01) | |
| *A61L 2/18* | (2006.01) | |
| *A01N 25/02* | (2006.01) | |
| *A01N 25/26* | (2006.01) | |

(52) U.S. Cl.
CPC ............. *A01N 59/16* (2013.01); *A01N 25/02* (2013.01); *A01N 25/22* (2013.01); *A01N 25/26* (2013.01); *A01N 25/30* (2013.01); *A01N 33/12* (2013.01); *A01N 59/00* (2013.01); *A61L 2/186* (2013.01); *A61L 2202/25* (2013.01)

(58) Field of Classification Search
CPC ........ A01N 25/02; A01N 25/22; A01N 25/26; A01N 25/30; A01N 33/12; A01N 59/00; A01N 59/16; A61L 2/186; A61L 2202/25
See application file for complete search history.

(56) References Cited

U.S. PATENT DOCUMENTS

| | | | | |
|---|---|---|---|---|
| 2003/0228373 | A1* | 12/2003 | Ludensky | ............... A01N 33/04 424/600 |
| 2006/0281663 | A1* | 12/2006 | Asmus | ..................... A61K 8/34 510/511 |
| 2009/0004287 | A1* | 1/2009 | Kimler | ................... A01N 59/00 424/616 |
| 2013/0177518 | A1* | 7/2013 | Nielsen | ..................... C11D 1/72 424/75 |

FOREIGN PATENT DOCUMENTS

| | | |
|---|---|---|
| CN | 103704264 B | 4/2014 |
| EP | 0059978 A1 | 9/1982 |
| EP | 1382666 A1 | 1/2004 |
| EP | 1557088 A1 | 7/2005 |
| WO | 91/08981 A2 | 6/1991 |
| WO | 2010/001319 A1 | 1/2010 |

OTHER PUBLICATIONS

Mckillop et al., "Sodium Perborate and Sodium Percarbonate: Cheap, Safe and Versatile Oxidising Agents for Organic Synthesis", Tetrahedron 51 (22): 6145-6166 (1995).

\* cited by examiner

*Primary Examiner* — Adam C Milligan
(74) *Attorney, Agent, or Firm* — Jeffrey N. Townes; Cozen O'Connor

(57) ABSTRACT

The present invention relates to a disinfectant composition comprising hydrogen peroxide and silver ions in association with at least one quaternary ammonium salt with biocidal action and compatible with silver ions. The composition can be used for disinfecting a room and any objects contained therein, in particular healthcare environments, such as, for example, laboratories, doctors' surgeries, hospital rooms, ambulance compartments and the like, where it is important to have a biocidal activity at low dosages proportional to the average contamination present.

9 Claims, 1 Drawing Sheet

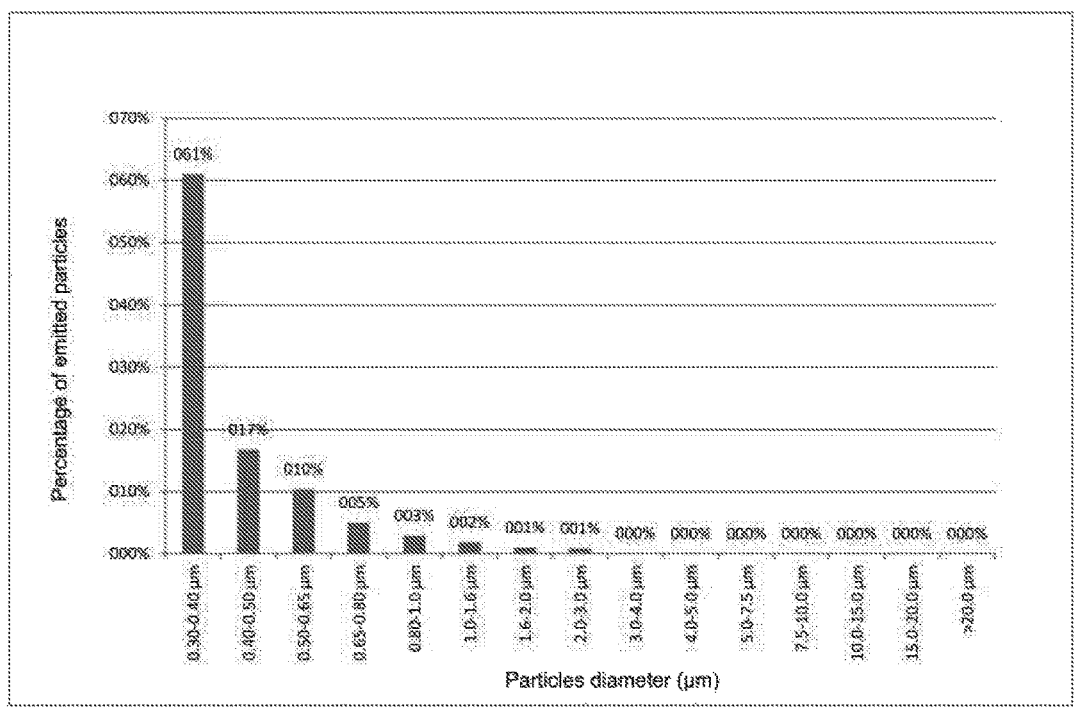

DISINFECTING COMPOSITION COMPRISING SILVER IONS AND A QUATERNARY SALT

CROSS-REFERENCE TO RELATED APPLICATIONS

This application is a national-stage application under 35 U.S.C. § 371 of PCT Application No. PCT/IB2015/055170, filed Jul. 8, 2015, which claims priority to Italian Patent Application No. MI2014A001251, filed Jul. 9, 2014, which are hereby incorporated by reference in their entirety.

The present invention relates in general terms to a disinfectant composition comprising hydrogen peroxide and silver ions in association with at least one quaternary ammonium salt with biocidal action and compatible with silver ions. The composition can be used for disinfecting a room and any objects contained therein, in particular healthcare environments, such as, for example, laboratories, doctors' surgeries, hospital rooms and ambulance compartments, as well as interior environments exposed to the public in general, such as public offices, nursing homes, schoolrooms, conference halls, motor vehicles in general, etc. where it is important to have a biocidal activity at low dosages proportional to the average contamination present.

BACKGROUND ART

In the field of disinfection, the use of aqueous solutions based on hydrogen peroxide and/or silver ions as disinfectant/antibacterial compositions is well known. EP1100341 discloses a method and a composition for treating plant matter and foodstuffs to prevent the deterioration thereof, which can also be used to eliminate or reduce the quantity of harmful organisms in growth media and water, as well as in workspaces, on surfaces etc. The method comprises the use of an aqueous solution comprising: hydrogen peroxide in a concentration of from 0.001% to 50%; dispersed metals or metal ions in a quantity ranging from 1 ppb to 5% with an effective concentration of metal ions selected from copper, zinc, nickel, iron, manganese, molybdenum, potassium and combinations thereof less than or equal to 2.5% and an effective concentration of silver ions less than or equal to 2.5%, as well as the possible addition of additives.

FR 2860721 discloses a method for treating a room by diffusion of a disinfectant liquid in the atmosphere of the room itself, following a precise operating sequence, so as to deliver a sufficient dose of liquid to obtain an effective treatment without going beyond the limits in terms of toxicity and allergenicity of the product.

WO2010001319 discloses a disinfectant composition comprising at least one non-ionic surfactant, in a mixture with silver ions and hydrogen peroxide, usable for disinfecting rooms, wherein non-ionic surfactants, such as, for example, ethoxylated alcohol, can be used.

Patent EP 059 978 A1 discloses a disinfectant composition for treating the water of swimming pools, comprising a copper or silver salt, in association with hydrogen peroxide and a quaternary ammonium salt (in particular a chloride). Compositions, suitable for dental use, in which use is made of cationic surfactants (quaternary ammonium salts), are also disclosed in patent application EP1557088, in which, however, citric acid is used as a stabilizing agent for the composition, or in patent application EP1382666.

There is also a known system called ASP Glosair™, in which use is made of an aqueous solution based on hydrogen peroxide and silver ions with bactericidal, virucidal and fungicidal activity, and which is diffused as a mist in the room using a diffusion device that, by exploiting a Venturi effect, makes it possible to obtain, under certain operating conditions (for example, rather long work times, substantial quantities of product delivered, mists with large drops, in the range of 8 to 12 microns), the formation of a sufficient concentration of oxidizing chemical species capable of destroying microorganisms.

However, there remains the problem of finding a disinfectant composition that has a high bactericidal and/or fungicidal, and/or sporicidal and/or virucidal power, associated with a large contact surface and is able to perform said action both in the short and long terms. The applicants have now found that it is possible to solve the aforesaid problem by means of an aqueous composition comprising hydrogen peroxide, silver ions and at least one suitable cationic surfactant that is compatible with the silver salt used and thus does not give rise to phenomena of precipitation of any adducts with the silver ion.

SUMMARY OF THE INVENTION

In a first aspect, the invention relates to a disinfectant aqueous composition comprising at least:

hydrogen peroxide, phosphate and/or hydrogen phosphate and/or phosphonate ions and at least one source of silver ions ($Ag^+$), and characterized in that it also comprises at least one quaternary ammonium salt compatible with silver ions, preferably selected from benzalkonium saccharinate and quaternary ammonium salts in general, provided that they have, as counterions, chemical species that do not give rise to interactions with the silver ions and in particular do not cause the precipitation of scarcely soluble compounds.

A further aspect of the present invention relates to the use of the aqueous composition according to the invention, as a disinfectant agent, preferably by diffusion by means of devices, in the form of a dry mist, steam, etc., or by spraying with manual dispensers or using the clean-in-place method (i.e. disinfection of devices and equipment without disassembling them).

A further aspect of the present invention relates to the use of the aqueous composition according to the invention as a disinfectant agent by spreading said composition with a suitable application means or by immersing the objects to be disinfected in said composition.

Furthermore, the present invention relates to a method for disinfecting a room, and the objects optionally contained therein, comprising the steps of:

(a) determining the volume of the room to be disinfected, preferably also evaluating the exposed surfaces based on the objects present in the room itself;

(b) determining, based on what was determined in the above step a), the optimal volumetric concentration of the disinfectant aqueous composition according to any one the preceding claims, to be delivered into the room;

(c) delivering said disinfectant aqueous composition into the room in the form of a dry mist, wherein 100% of the particles making up said dry mist have a diameter less than or equal to 3 microns and at least 50% have a diameter less than or equal to 0.40 microns.

DETAILED DESCRIPTION

Additional features and advantages of the present invention will become more apparent from the detailed description that follows and the example embodiments, also with reference to the appended figures.

FIG. 1 shows a graphic representation of the percentage distribution of the particles of the disinfectant composition emitted during disinfection of a closed room performed according to the method of the invention.

In the present description and in the appended claims the concentration of the components comprised in the disinfectant solution is expressed in grams (or milligrams) of the component per Kg of final solution (g/Kg or mg/Kg).

The term "$C_1$-$C_{22}$ alkyl group" indicates an alkyl residue comprising from 1 to 22 carbon atoms, linear or branched, optionally substituted, for example with phenyl, carbonyl, ester or ether groups or the like.

"Linear or branched $C_1$-$C_4$ alcohol" indicates an organic alcohol compound having from 1 to 4 carbon atoms, for example selected from: methanol, ethanol, propanol, isopropanol and the like.

The term "aryl group" indicates an aromatic residue with 6 carbon atoms, possibly substituted with alkyl, ester or ether groups.

The term "degree of ethoxylation" EO (or "degree of propoxylation" OP) indicates the number of moles of ethoxide —($CH_2CH_2O$)— (or of propoxide —$CH_2CH$ ($CH_3$)—O—) present in one mole of epoxylate (and/or propoxylate) derivative.

The term "fatty alcohols" indicates straight-chain aliphatic alcohols having from 8 to 24 carbon atoms.

"Quaternary ammonium salt compatible with silver ions" indicates an ammonium salt capable of being mixed in the present composition without causing any substantial precipitations due to the interaction between said salt and the silver ions.

The ammonium salt has nitrogen atom holding a positive charge, possibly substituted with one or more aliphatic and/or aromatic $C_1$-$C_{22}$ functional groups, and is characterized in that it has a counterion which permits the presence of the ammonium derivative and silver salt within the composition of the invention in the form of an aqueous solution, without giving rise to precipitation phenomena, as would occur if the counterion were not compatible with the silver ions, for example a chloride counterion ($Cl^-$) or the like.

The term "aqueous solution" is meant to indicate a liquid composition obtained by dissolving or mixing the various components in water, said solution being devoid of residues due, for example, to precipitates, suspensions and the like.

The term "deionized water" indicates water from which the saline component has been extracted and preferably having a conductivity ≤0.1 μS/cm.

The term "disinfectant agent" is meant to indicate an agent endowed with bactericidal, virucidal, sporicidal, fungicidal and/or mycobactericidal properties, particularly suitable for the treatment of interior environments such as rooms, premises and the like, including any objects contained therein.

The term "dry mist" is meant to indicate a mist that does not wet the surfaces it is placed in contact with. In order for an airborne dispersion of drops to behave like a dry mist, said mist must have a particle size of less than 10 microns.

As mentioned above, the present composition is characterized in that it contains at least one quaternary ammonium salt which, in association with the hydrogen peroxide and the silver ions (Ag+), is surprisingly capable of imparting to the composition strong disinfectant properties associated with a rapid speed of action, while ensuring the absence of settling materials or precipitates due to the interaction between the anionic component and the silver ions. The composition of the invention is thus suitable for disinfecting rooms and any objects contained therein, such as, for example, hospitals, out-patient clinics, operating rooms and, in general, healthcare environments in which it is necessary to have a high degree of disinfection proportional to the average microbial contamination.

According to one variant, the composition of the invention is characterized in that it comprises a dry residue in an amount less than or equal to 0.5% by weight, preferably in an amount less than or equal to 0.3%.

In the present disinfectant composition, preferred quaternary ammonium salts are made up of a cationic nitrogen atom substituted with $C_1$-$C_{22}$ alkyl or alkylaryl groups, identical to or different from one another. Said cationic nitrogen atom has a counterion compatible with the silver ion, and is preferably selected from saccharinate, nitrate, phosphate, carbonate, bicarbonate, propionate and hydroxide and in any case such as not to cause precipitations.

The present invention thus relates to an aqueous composition comprising: hydrogen peroxide, phosphate and/or hydrogen phosphate and/or phosphonate ions and at least source of silver ions ($Ag^+$), and characterized in that it further comprises at least one quaternary ammonium salt compatible with silver ions, containing $C_1$-$C_{22}$ alkyl and/or alkylaryl groups, identical to or different from one another, said quaternary ammonium salt having a counterion selected from saccharinate, nitrate, phosphate, carbonate, bicarbonate, propionate and hydroxide.

In one embodiment, said at least one ammonium salt is selected from benzalkonium saccharinate, benzalkonium nitrate, didecyl methyl ammonium carbonate, didecyl methyl ammonium bicarbonate, didecyl methyl polyoxyl ethyl ammonium propionate and mixtures thereof, preferably from benzalkonium saccharinate, didecyl methyl polyoxyl ethyl ammonium propionate and mixtures thereof.

The benzalkonium ion appears as a heterogeneous mixture of alkyl dimethyl benzyl ammonium ions, wherein said alkyl group is a linear alkyl group containing from 8 to 18 carbon atoms, preferably containing an even number of carbon atoms. Benzalkonium saccharinate (alkyl dimethyl benzyl ammonium saccharinate—CAS No 68989-01-5), wherein the linear alkyl group contains from 12 to 18 carbon atoms, is particularly preferred. Benzalkonium saccharinate is commercially available.

With regard to the propionate derivative, N,N-didecyl-N-methyl-(polyoxyl ethyl) ammonium propionate—CAS 94667-33-1, likewise commercially available, is particularly preferred.

The at least one quaternary ammonium salt can be present in the composition in amounts comprised between 0.01 and 50 g/Kg of solution, values comprised between 200 and 800 mg/Kg being particularly preferred. If the aqueous composition comprises a mixture of quaternary ammonium salts, said amount refers to the total amount of ammonium salts comprised in the composition.

The applicants have surprisingly found that the presence of at least one quaternary ammonium salt, as described above, together with Ag+ ions in adequate concentrations and hydrogen peroxide, impart to the disinfectant solution of the invention further strong disinfectant properties. In this regard, the present composition shows an excellent biocidal effectiveness, especially against mould and yeast, while assuring a prolonged time of contact on surfaces and thus prolonging the biocidal and biostatic action, even beyond normal treatment times. Moreover, the rapidity of action is also particularly convenient.

The composition of the invention further comprises a source of silver ions (Ag+), preferably in the form of a salt selected from nitrate, citrate or hydroxide, silver nitrate being particularly preferred.

The source of Ag+ ions is present in the composition in an amount comprised between 10 and 200 mg of Ag+ ion source per Kg of solution, amounts between 50 and 150 mg/Kg being particularly preferred.

Hydrogen peroxide is used in the composition of the present invention in a concentration comprised between 5 and 200 g/Kg, preferably between 10 and 100 g/Kg, more preferably between 30 and 100 g/Kg, even more preferably between 60 and 80 g/Kg. The hydrogen peroxide that is utilizable (stabilized) can be easily found on the market, for example in the form of food grade or cosmetic grade $H_2O_2$.

The phosphate ($PO_4^{3-}$), hydrogen phosphate ($HPO_4^{2-}$ and/or $H_2PO_4^-$) and/or phosphonate ions, the latter mostly deriving from hydroxyethylidene diphosphonic acid, HEDP or editronic acid, of the formula:

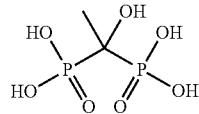

can be present in the composition of the invention in an amount comprised between 50 and 2000 mg/Kg, preferably between 100 and 500 mg/Kg of solution, more preferably between 100 and 200 mg/Kg. Said phosphate ($PO_4^{3-}$), hydrogen phosphate ($HPO_4^{2-}$ and/or $H_2PO_4^-$) and/or phosphonate ions can be introduced into the present disinfectant composition by adding: a phosphate salt and/or acid, alkaline or alkaline earth phosphate, a water-soluble diphosphonic acid or derivative, phosphoric acid ($H_3PO_4$) or mixtures thereof. In the case of the phosphate ion, it can be introduced into the composition also as a counterion of the ammonium salt. In a preferred embodiment, the composition of the invention comprises hydroxyethylidene diphosphonic acid and/or $KH_2PO_4$, even more preferably in total amounts comprised between 150 and 300 mg/Kg of solution, preferably between 100 and 200 mg/Kg.

In this regard, it is believed that the phosphate and/or hydrogen phosphate and/or phosphonate ions perform a stabilizing effect for hydrogen peroxide. In particular, the introduction of said ions makes it possible to adjust the pH in an optimal manner with the formation of a buffered solution with an acidic pH, at a value whereby the hydrogen peroxide is more stable and has a particularly high oxidizing capacity. Therefore, in one embodiment of the invention, the pH of the disinfectant composition is adjusted to values of less than 5, even more preferably comprised from 1 to 4, values comprised from 2 to 3 being particularly preferred. The pH adjustment can be achieved by adding at least one phosphoric derivative as described above and/or by adding carboxylic acids, for example citric acid.

Surprisingly, and contrary to what occurs following the association of a common quaternary ammonium salt (for example in the form of a chloride) with a silver ion, the present composition serves to even further increase the biocidal and disinfectant action both of hydrogen peroxide and silver ions, as well as of the cationic salt itself. The present composition is in fact capable of remaining in the form of a stable aqueous solution over time, substantially without the formation of compromising precipitates or settling bodies which typically result from the association of the quaternary ammonium salt with the Ag+ ions. Thanks to its stability, the composition of the invention is capable of showing both a short-term and long-term antibacterial disinfectant effect. The presence of the Ag+ ions imparts a long-term biocidal action to the composition, whilst the ammonium salt performs a relatively short-term biocidal action.

The presence of any surfactants such as the ethoxylated and/or propoxylated compounds described below, ensures, moreover, a high wettability of the composition of the invention and effectiveness of action, which make the present composition particularly advantageous and convenient. In this regard, and according to one embodiment, the composition of the invention may also comprise at least one ethoxylated and/or propoxylated derivative having a degree of ethoxylation EO and/or propoxylation OP comprised between 4 and 40 mol, preferably between 4 and 22. Preferably, the present disinfectant aqueous composition comprises a mixture of ethoxylated alcohols having from 8 to 18 carbon atoms ($C_8$-$C_{18}$). By way of example, "ethoxylated derivative 20 mol EO" indicates a fatty alcohol made to react with 20 moles of ethylene oxide.

According to a further variant, the composition according to the invention can comprise, in addition to the components specified above, at least one ethoxylated and/or propoxylated $C_{10}$-$C_{18}$ alcohol, 4-40 mol EO/OP.

In a further embodiment, the composition comprises 50-600 mg/Kg of at least one ethoxylated alcohol selected from C10 ethoxylated alcohols, 6 mol EO, C13 ethoxylated alcohols 8 mol EO and mixtures thereof in combination with 5-60 mg/Kg, preferably 10-40 mg/kg, of glucosidic surfactants (for example coco glucosides, i.e. C8-C16 hydrocarbons bound to glucose oligomers with an ether bond), optionally also with 10-20 mg/kg of sorbitan monolaurate 20 mol EO.

The applicants have found that the presence of said mixture contributes to improving the process of nebulizing the disinfectant solution, permitting a larger contact surface, homogeneous diffusion and smaller dosages in the case of spray applications. The ethoxylated and/or propoxylated derivatives are can be present in the composition in an amount comprised between 20 and 1000 mg/Kg, even more preferably comprised between 200 and 600 mg/Kg of solution, most preferably between 200 and 500 mg/Kg.

The present composition can further comprise a $C_1$-$C_4$ alcohol, for example selected from ethanol, propanol, and preferably isopropanol. Said alcohol is generally premixed with the selected ammonium salt, thus enhancing solubility in the aqueous environment of the composition of the invention.

Said alcohol can be present in the disinfectant composition of the invention in an amount comprised between 0.5 and 100 g/Kg, preferably between 0.5 and 50 g/Kg, more preferably between 0.5 and 4 g/Kg of solution.

Optionally, the present composition can also contain at least one organic $C_1$-$C_{12}$ aliphatic and/or aromatic acid, for example salicylic acid and/or citric acid, preferably in an amount comprised between 10 and 500 mg/Kg of solution. Said acid is useful for further enhancing the biocidal/biostatic effect of the product.

The composition of the invention can also comprise complexing or sequestering agents, for example phosphonic, amino and/or gluconic ones, and possibly surfactants, typically from carbohydrates, such as coco glucoside and the like. The preferred complexing agents are selected from: gluconic acid, EDTA, DTPA and phosphonic acids. Sequestering agents exert their action on the material subject to treatment, in particular on the membranes of microorganisms. In fact, said sequestering agents act upon the protein component, on the one hand, and denature the complex structures protecting microorganisms in general on the other.

Therefore, in one embodiment, the present composition comprises the following components in the following amounts:

| | |
|---|---|
| Source of silver (Ag+) ions | 10-200 mg/kg |
| | preferably 20-200 mg/Kg |
| Quaternary ammonium salt | 0.1-50 g/kg |
| compatible with the Ag+ ions | preferably 0.1-10 g/Kg, |
| | more preferably 0.1-5 g/Kg |
| $H_2O_2$ | 5-100 g/kg |
| | preferably 20-100 g/Kg |
| Alcohol $C_1$-$C_4$ | 1-100 g/kg |
| | preferably 1-50 g/Kg |
| Aliphatic and/or aromatic organic acids | 0-500 mg/kg |
| Complexing agents | 0-3,000 mg/kg |
| | preferably 100-500 mg/Kg |
| Ethoxylated and/or propoxylated alcohols | 100-800 mg/kg |
| | preferably 100-600 mg/Kg |
| Deionized water | q.s. to 1 kg |
| Phosphoric acid | q.s. to pH 1-5 |

In a further embodiment, the present composition comprises:

| | |
|---|---|
| Silver nitrate | 60-120 mg/kg |
| Benzalkonium saccharinate | 200-800 mg/kg |
| Isopropyl alcohol | 2-8 g/kg |
| Citric acid | 20-100 mg/kg |
| | preferably 10-40 mg/Kg |
| Hydroxy ethylidene diphosphonic acid | 100-300 mg/kg |
| | preferably 100-200 mg/Kg |
| Disodium EDTA | 50-100 mg/kg |
| Ethoxylated C10 alcohol, 6 mol EO | 300-600 mg/kg |
| | preferably 300-500 mg/Kg |
| Coco glucoside | 5-60 mg/kg |
| | preferably 5-50 mg/Kg |
| $H_2O_2$ | 60-80 g/kg |
| Deionized water | q.b. a 1 kg |
| Phosphoric acid | q.s. to pH 2-3 |

The composition of the invention in the form of an aqueous solution can be prepared by means of a process that entails adding the source of Ag+ ions and the quaternary ammonium salt to a preliminary amount of deionized water, to which the hydrogen peroxide is subsequently added. Finally, the phosphate and/or hydrogen phosphate and/or phosphonate ions and, optionally, deionized water are added to reach the volume.

According to a first variant, the aqueous composition can be prepared by means of a process that entails premixing the suitable quaternary ammonium salt with the selected $C_1$-$C_4$ alcohol. This serves to facilitate the solubilization of the ammonium salt, particularly in the case of the saccharinate, in the aqueous environment of the composition.

Therefore, in a further aspect, the present invention relates to a process for preparing the disinfectant composition described above, comprising the steps of:
 a. mixing deionized $H_2O$ with the auxiliary components (complexing agents, surfactants, etc.)
 b. adding to the deionized water a source of Ag+ ions and the compatible quaternary ammonium salt, the latter possibly premixed with a $C_1$-$C_4$ alcohol;
 c. adding $H_2O_2$,
 d. adjusting the pH to values lower than 5, preferably by adding phosphoric acid and water.

Preferably, said steps are carried out in the order specified above, so as to obtain the composition of the invention in accordance with the preferred embodiments described above.

Advantageously, the aqueous disinfectant solution obtained has a high biocidal power, a high rapidity of action and very little dry residue. The dry residue, in particular, can be less than 3 g/Kg.

The present composition is further characterized in that it does not comprise ions of heavy metals such as copper, zinc and the like and may be easily applied also on a large scale, while substantially avoiding the typical toxicological problems that can derive from the presence of said metals.

Furthermore, in the present composition the absence of halide ions and chlorides in particular takes on particular importance, as it minimizes the corrosive effects of the latter, especially on objects made of metal, including stainless steel.

In one embodiment, the composition of the invention comprises an amount of hydrogen peroxide less than or equal to 3% p/p (30 g/Kg) relative to the total weight, preferably in an amount comprised between 5 and 30 g/Kg, thus permitting it to be formulated also as a gel. Said formulation can be prepared by associating the composition with gelling agents known in the art. The use of the present composition in the form of a gel or dry mist or by applying it with manual sprayers makes possible a vast range of applications of the present composition as a biocidal, antibacterial and biostatic agent.

According to a further aspect, the present invention relates to the use of the aqueous composition as previously defined as a bactericidal, virucidal, sporicidal, fungicidal and/or mycobactericidal agent.

A further aspect of the invention relates to a method for disinfecting a room and any objects optionally contained therein, which comprises the steps of:
 (a) determining the volume of the room to be disinfected, evaluating the exposed surfaces based on the objects present in the room itself;
 (b) determining, based on what was determined according to the above step a), the optimal volumetric concentration of the present disinfectant aqueous composition to be delivered into the room;
 (c) delivering said disinfectant aqueous composition into the room in the form of a dry mist, wherein 100% of the particles making up said dry mist have a diameter less than or equal to 3 microns and at least 50% have a diameter less than or equal to 0.40 microns.

According to a first variant of the method according to the invention, before step a) a further step i) can be carried out, with the aim of determining the type and degree of contamination of the room by microorganisms, in order to modulate the treatment in the most appropriate manner, thus optimizing the amount to be delivered based on the parameters determined.

The determination of the type and degree of contamination of the room to be disinfected, and of the effectiveness of the disinfection treatment, can be based on methods—well known in the art—of culturing the microorganisms of interest so as to make a count of the viable microorganisms, expressed as $CFU/cm^2$.

The effectiveness of the disinfection treatment according to the invention can be determined as indicated below.

Based on experiments conducted by the applicant, it was found that the volumetric concentration of the disinfectant aqueous composition of step b) can be comprised between about 0.5 ml/m$^3$ and 30 ml/m$^3$, more preferably between about 1 ml/m$^3$ and 10 ml/m$^3$.

Delivery into the room according to step c) can be conducted, for example, with a spraying device used in the art, and capable of obtaining a dry mist in which 100% of the particles have a diameter less than or equal to 3 microns and at least 50% of the particles have a diameter less than or equal to 0.40 microns. According to a further preferred variant, at least 95% of the particles emitted in step c) in the form of a dry mist have a diameter less than or equal to 1 microns and at least 50% by weight, preferably at least 60% by weight, of the particles have a diameter less than or equal to 0.4 microns. The percentage of particles having a given diameter is expressed as a numerical percentage; the number and size of the particles are measured as described below. Delivering particles having sizes comprised in the above-mentioned intervals into the room makes it possible to avoid the phenomenon of mist drop-off (rapid condensation of the mist into drops of a larger size which fall to the floor), thus favouring a homogeneous diffusion of the particles making up the dry mist in the air and a uniform deposit thereof on the surfaces undergoing treatment.

Preferably, the speed of delivery of said dry mist is comprised between about 70 m/sec and 90 m/sec. The diffusion pressure during step c) is usually calibrated in such a way as to obtain a temperature of the disinfectant solution sprayed in the form of a dry mist preferably comprised between about 5° C. and about 40° C.

In step c) the dry mist can be delivered at a flow rate comprised between 15.0-20.0 ml/min.

According to one variant of the method of the invention, the time of spraying the solution during step c) is less than about 10 minutes, preferably comprised from about 1 to 10 minutes, more preferably from about 2 to 7 minutes. Said variant of the method according to the invention is preferably applied to the treatment of healthcare environments (ambulances, clinics, patient wards, operating rooms, etc.).

According to one variant, the method according to the invention comprises a further step (d), in which the disinfectant composition in the form of a dry mist is kept in contact with the room, and any objects contained therein, for a pre-established time, so as to achieve the desired level of disinfection. When present, said step (d) can have a duration comprised between about 5 and about 180 minutes, preferably 5-120 minutes.

The method according to the invention, which envisages the delivery of particles of the disinfectant composition having the above-described size, assures an effective disinfection of rooms and the objects contained therein in a short time, at low dosages and in a homogeneous manner.

This also enables the disinfection of a room and of the objects contained therein to be repeated several times in the space of a day, for example after every use compromising the degree of microbial contamination thereof. This possibility is particularly advantageous in the disinfection of environments repeatedly subject to microbial contaminations, for example operating rooms and hospital rooms or the interiors of ambulances.

Furthermore, thanks to the deposition of the constituent particles of the dry mist on the surfaces present in the disinfected room, when it is applied according to the above-described method, the disinfectant aqueous composition of the invention exerts both a short-term and long-term biocidal and/or biostatic activity, preventing and/or slowing down the phenomena of microbial recontamination between one disinfectant treatment and another.

The present invention will now be described with the following non-limiting experimental part.

EXPERIMENTAL PART

Measurement Methods

Dry residue: about 100-200 g of a sample of disinfectant composition is carefully weighed out in a wide, suitably sized capsule. The sample is placed in a temperature-controlled oven at 105°±2° C. for at least 3 hours. The sample is subsequently allowed to cool to room temperature in a silica gel dryer and the residual weight is determined.

Effectiveness of disinfection treatment/degree of contamination: Method AFNOR NF T 72-281, May 2009.

Number and diameter of the particles: measured with a Grimm spectrometer Mod. 1.108.

Example 1: Preparation of the Composition of the Invention (AgQ)

With reference to the preparation of 1 Kg of product:

1—Premix 500 mg of benzalkonium saccharinate with 5 g of isopropyl alcohol;

2—Premix 100 g of silver nitrate with about 50 mL of deionized water

3—In a 1 litre container add, under stirring and in the order specified, to about 700 mL of deionized water:

Citric acid (40 mg); hydroxyethylidene diphosphonic acid (200 mg); Disodium EDTA (80 mg/kg); Ethoxylated alcohol C10, 6 mol EO (400 mg/kg); Coco Glucoside (10 mg)

the saccharinate solution (1);

the silver nitrate solution (2);

approx. 230 g about of hydrogen peroxide 130 Vol (so as to reach a final concentration of 76 g/L).

4—Adjust the pH by adding 1-2 g of phosphoric acid.

5—Transfer into a dark container and keep in a cool place away from sources of light until the time of use.

Example 2: Use of the Composition of the Invention AgQ as an Antibacterial Agent The test was performed on about $5\times10^3$ colonies of *Staphylococcus aureus* 6538 by spraying the composition AgQ prepared in Example 1.

The composition was sprayed for 3 minutes in the form of a dry mist in a completely closed room of 55 $m^3$ at a volumetric concentration of 1 $ml/m^3$. Thirty minutes after the end of delivery of the composition, the reduction in bacterial colonies resulting from the treatment was determined.

The data obtained are summarized in Table 1, which shows the reduction values expressed in logarithmic percentage terms.

For the purposes of comparison, the same Table 1 shows the reduction values following a treatment carried out according to the same method as described above, using the following aqueous compositions:

Q (comparison): biocidal aqueous composition containing 76 g/Kg of hydrogen peroxide and 0.5 g/Kg of benzalkonium chloride.

C (comparison): biocidal aqueous composition containing 76 g/Kg of hydrogen peroxide and 100 g/Kg of silver nitrate.

TABLE 1

| | Logarithmic Reduction | % reduction | Increase in reduction compared to C |
|---|---|---|---|
| AgQ | 3.25 | 87.80 | 47.60% |
| Q (comp.) | 2.65 | 71.60 | 20.30% |
| C (comp.) | 2.20 | 59.50 | — |

As can be seen from the table, the composition AgQ of the invention shows a decidedly better action than both composition 0 (comprising hydrogen peroxide and an ammonium quaternary chloride), and composition C (comprising hydrogen peroxide and silver ions).

Example 3: Determination of the Number and Diameter of the Dry Mist Particles

While the composition AgQ prepared in Example 1 was being sprayed under the conditions described in Example 2, samples were taken of the airborne particles to determine the number and size of the particles emitted. The data (number and size of the mist particles) were acquired by means of a Grimm spectrometer Mod. 1.108 throughout the delivery of the disinfectant composition, with a measurement taken every 6 seconds.

FIG. 1 shows the percentage distribution of the number of particles emitted according to their diameter.

The graph shows that over 60% of the particles diffused in dry mist form have dimensions falling within the interval of 0.30-0.40 µm and that 96% of the diffused particles have a diameter of less than 1.00 µm. Furthermore, 100% of the diffused particles have a diameter of less than 3.00 µm.

The invention claimed is:

1. An aqueous composition consisting of:
hydrogen peroxide,
hydroxyethylidene diphosphonic acid and/or $KH_2PO_4$,
at least one source of silver ions ($Ag^+$),
didecyl methyl polyoxyl ethyl ammonium propionate,
at least one ethoxylated alcohol selected from $C_{10}$ ethoxylated alcohols, $C_{13}$ ethoxylated alcohols and mixtures thereof,
salicylic acid and/or citric acid,
isopropanol,
complexing agents selected from the group consisting of gluconic acid, EDTA, DTPA and phosphonic acids,
glucosidic surfactants, and
sorbitan monolaurate;
wherein said aqueous composition is in the form of a dry mist, and wherein 100% of the particles making up the dry mist have a diameter of less than or equal to 3 microns, and wherein at least 50% of the particles making up the dry mist have a diameter of less than or equal to 0.40 microns.

2. The aqueous composition according to claim 1, wherein said didecyl methyl polyoxyl ethyl ammonium propionate is present in amounts between 0.01 and 50 g/Kg.

3. The aqueous composition according to claim 1, wherein said at least one source of silver ions (Ag+) is a salt, selected from nitrate, hydroxide and citrate, present in amounts between 10 and 200 mg/Kg.

4. The aqueous composition according to claim 1, wherein the hydrogen peroxide is present in amounts between 5 and 200 g/Kg.

5. The aqueous composition according to claim 1, wherein
the ethoxylated alcohol is present in an amount ranging from 50-600 mg/Kg and selected from $C_{10}$ ethoxylated alcohols, $C_{13}$ ethoxylated alcohols and mixtures thereof,
the glucosidic surfactants are present in an amount ranging from 5-60 g/Kg, and
the sorbitan monolaurate is present in an amount ranging from 10-20 g/kg.

6. The composition according to claim 2, wherein the didecyl methyl polyoxyl ethyl ammonium propionate is present in amounts between 200 and 800 mg/Kg.

7. The composition according to claim 3, wherein the at least one source of silver ions (Ag+) is $AgNO_3$, present in amounts between 50 and 150 mg/Kg.

8. The composition according to claim 4, wherein the hydrogen peroxide is present in amounts between 60 and 80 g/Kg.

9. An aqueous composition consisting of:

| | |
|---|---|
| Silver nitrate | 60-120 mg/kg |
| Benzalkonium saccharinate | 200-800 mg/kg |
| Isopropyl alcohol | 2-8 g/kg |
| Citric acid | 20-100 mg/kg |
| Hydroxyethylidene diphosphonic acid | 100-300 mg/kg |
| Disodium EDTA | 50-100 mg/kg |
| Ethoxylated C10 alcohol, 6 mol EO | 300-600 mg/kg |
| Coco glucoside | 5-60 mg/kg |
| $H_2O_2$ | 60-80 g/kg |
| Deionised water | q.s. to 1 kg |
| Phosphoric acid | q.s. to pH 2-3. |

\* \* \* \* \*